US00PP26553P3

(12) United States Plant Patent
Korlipara et al.

(10) Patent No.: US PP26,553 P3
(45) Date of Patent: Mar. 29, 2016

(54) ***LITHODORA* PLANT NAMED 'CRYSTAL BLUE'**

(50) Latin Name: *Lithodora diffusa*
Varietal Denomination: Crystal Blue

(71) Applicant: Terra Nova Nurseries, Inc., Canby, OR (US)

(72) Inventors: Harini Korlipara, Canby, OR (US); John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 128 days.

(21) Appl. No.: 14/120,893

(22) Filed: Jul. 8, 2014

(65) Prior Publication Data
US 2016/0014944 P1 Jan. 14, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Lithodora* plant characterized by large sky blue flowers, a compact, spreading, low mounding habit, excellent dense branching with flower clusters at the end of every branch, dark green leaves, excellent vigor, and good garden performance.

1 Drawing Sheet

Botanical denomination: *Lithodora diffusa.*
Variety designation: 'Crystal Blue'.

BACKGROUND OF THE INVENTION

The present invention relates to a new and distinct cultivar of *Lithodora*, given the name, 'Crystal Blue'. *Lithodora* is in the family Boraginaceae. This new cultivar was found as a naturally occurring branch mutation of *Lithodora diffusa* 'White Star', U.S. Plant Pat. No. 20,078.

Compared to the mother plant, *Lithodora diffusa* 'White Star' the new cultivar has sky blue flowers rather than bicolor blue and white colored flowers.

Compared to the other blue *Lithodora diffusa* on the market, the new cultivar has sky blue rather than deep blue, medium blue or bicolor flower color. The new cultivar has larger flowers than the others on the market.

The new cultivar is unique in its large flower size and sky blue flower color. In addition it exhibits the following characteristics:

1. a compact, spreading, low mounding habit,
2. excellent dense branching with flower clusters at end of every branch,
3. dark green leaves,
4. excellent vigor, and
5. good garden performance.

The new variety has been reproduced only by asexual propagation (stem cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a bed of two-year-old *Lithodora* 'Crystal Blue' growing in the trial field in April in Canby, Oreg.

FIG. 2 shows a close up of the flower.

DETAILED PLANT DESCRIPTION

The following is a detailed description of the new *Lithodora* cultivar based on observations of two-year-old specimens in April grown outside in the ground in the trial beds in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Spreading.
*Type.*—Evergreen, mat forming subshrub/perennial/groundcover.
*Cold hardiness.*—USDA Zone 5a-8.
*Size.*—Grows to 52 cm wide and 22 cm tall to the top of the foliage.
*Vigor.*—Excellent.
*Branching.*—Extremely well branched.
*Stem.*—Grows to 23 mm long, pubescent, internodes range from 3 mm to 7 mm long, Yellow Green 145B; older woody stems grow to 3 mm wide, Brown 200A.
*Roots.*—Fibrous, freely branching, plants root easily from stem tip cuttings.

Leaf:

*Type.*—Simple.
*Arrangement.*—Alternate.

*Blade size*.—Grow to 22 mm long and 10 mm wide.
*Petiole description*.—Sessile.
*Shape*.—Linear lanceolate.
*Venation*.—Pinnate.
*Margins*.—Revolute.
*Apex*.—Acute.
*Base*.—Truncate.
*Surface texture*.—Pubescent of both sides.
*Leaf color*.—Top side Yellow Green 147A including vein, bottom side Yellow Green 147B including vein.

Inflorescence:
*Type*.—Terminal cyme.
*Number of flowers*.—3 to 6 per cyme.
*Size of inflorescence*.—Spreads 4.5 cm wide and 2.5 cm deep.
*Peduncle*.—4 mm long and 1.5 mm wide, pubescent, Yellow Green 145C.
*Pedicel*.—None.
*Bloom period*.—Middle of April to middle of May in Canby, Oreg.

Flower bud:
*Size*.—16 mm long and 5 mm wide at the widest point prior to opening.
*Description*.—Tubular.
*Surface texture*.—Pubescent.
*Color*.—Purple 75A with Purple 79C on midribs.

Flower:
*Type*.—Regular.
*Shape*.—Rotate to salverform.
*Corolla description*.—20 mm wide and 19 mm deep; tube 7 mm long and 2 mm to 3.5 mm wide, 5 lobes, each lobe 10 mm long and 6 mm wide (connecting on the bottom 3 mm), oblong, margins entire and slightly undulate, tips obtuse, lobes top side Blue 101B with the midrib Blue 102D and the margins Blue 106D, bottom side Blue 100B with midrib 101A to Violet Blue 93B and margins Blue 104D; tube Blue 100A on top blending to Purple N79B on bottom.
*Calyx description*.—Campanulate, 3 mm wide and 10 mm deep, 5-lobed, lobes linear lanceolate, tips acuminate, margins entire, Green 137A and pubescent on both sides.
*Pistil description*.—1, 18 mm long, ovary 4 lobed and about 1 mm long and 2 mm wide, style 17 mm long, White NN155C, stigma Purple 79A.
*Stamen description*.—5, filaments 1.5 mm long and White NN155D, anthers 2.5 mm long and Greyed Yellow 162B, pollen White 155B.
*Fragrance*.—None.
*Lastingness*.—A cyme blooms for about 2 weeks on the plant.

Seed: Nutlets, none seen.

Pests and diseases: *Lithodora* have no major pests or disease problems. This plant has shown no special disease or pest resistance in Canby, Oreg.

We claim:

1. A new and distinct form of *Lithodora* plant substantially as shown and described.

* * * * *

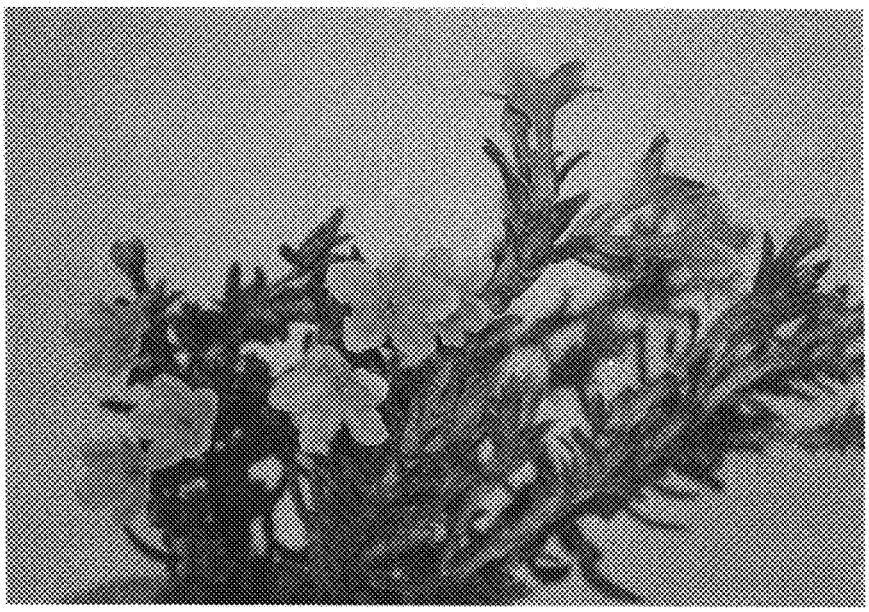

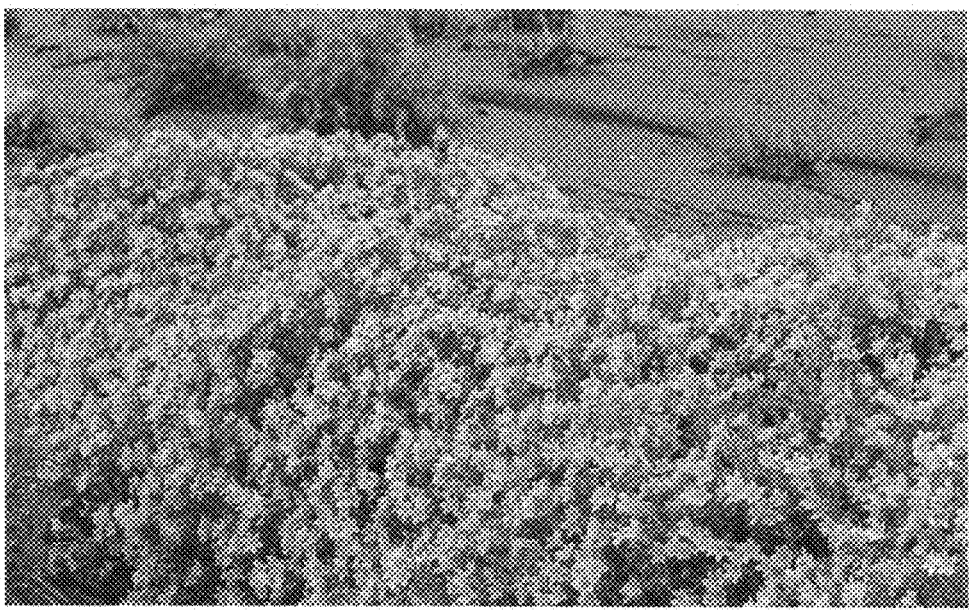
FIG. 1 above, FIG. 2 below